United States Patent [19]

Cohen et al.

[11] Patent Number: 5,241,867
[45] Date of Patent: Sep. 7, 1993

[54] METHOD AND APPARATUS FOR APPORTIONING A PRIMARY VOLUME OF FLUID INTO A DETERMINED NUMBER OF SECONDARY VOLUMES HAVING A PREDEFINED MUTUAL RELATIONSHIP

[75] Inventors: Daniel Cohen; Yves Le Gall; Jean Dausset, all of Paris; Philippe Millasseau, Epinay; Isabelle Le Gall, Paris, all of France

[73] Assignee: Bertin et Cie, Plaisir Cedex, France

[21] Appl. No.: 882,753

[22] Filed: May 11, 1992

Related U.S. Application Data

[63] Continuation of Ser. No. 696,261, Apr. 30, 1991, abandoned, which is a continuation of Ser. No. 347,958, filed as PCT/FR88/00365, on Jul. 8, 1988, abandoned.

[30] Foreign Application Priority Data

Jul. 10, 1987 [FR] France ............... 87 09891

[51] Int. Cl.⁵ .............................. G01N 1/20
[52] U.S. Cl. .................. 73/863.41; 137/561 A
[58] Field of Search ........... 73/863.41, 863.51, 863.52; 137/561 A

[56] References Cited

U.S. PATENT DOCUMENTS 1,100,649  6/1914  Bennett et al. ................. 137/561 A
3,848,633 11/1974  Nurtig et al. .
3,864,938  2/1975  Hayes, Jr. ...................... 137/561 A
4,126,043 11/1978  Schurmann .
4,256,140  3/1981  Swaroop et al. ............... 137/561 A
4,284,243  8/1981  Shaner .......................... 137/561 A
4,536,104  8/1985  Bungert ........................ 137/561 A
4,565,216  1/1986  Meier ............................ 137/561 A
4,771,641  9/1988  Beltrop ........................... 73/863.52

FOREIGN PATENT DOCUMENTS 1034886  9/1952  Fed. Rep. of Germany .
2157643  5/1973  France .
2372578  6/1978  France .
2463407  2/1981  France .

Primary Examiner—Robert Raevis
Attorney, Agent, or Firm—Browdy and Neimark

[57] ABSTRACT

A method and apparatus for apportioning a primary volume of fluid into a plurality of secondary volumes having a predefined mutual relationship, by means of a chamber for receiving the primary volume of fluid having a bottom including fluid evacuation orifices (6) disposed in a common horizontal plane and connected to evacuation ducts (8) provided with cocks (19), enabling the beginning of fluid flow in the ducts (8) to be synchronized, with the end of said flow being determined by the free surface (26) of the fluid being fractioned by the evacuation orifices (6).

14 Claims, 4 Drawing Sheets

METHOD AND APPARATUS FOR APPORTIONING A PRIMARY VOLUME OF FLUID INTO A DETERMINED NUMBER OF SECONDARY VOLUMES HAVING A PREDEFINED MUTUAL RELATIONSHIP

This application is a continuation of application Ser. No. 07/696,261, filed Apr. 30, 1991, now abandoned, which is a continuation of application Ser. No. 07/347,958, filed as PCT/FR88/00365, on Jul. 8, 1988, now abandoned.

The invention relates essentially to a method and to apparatus for apportioning a primary volume of a fluid, in particular of a liquid, into a determined number of secondary volumes having a predefined mutual relationship.

It is well known that, in order to apportion fluids into predefined volumes, various different methods may be used, with the most common of them being entirely mechanical and making use of volumes which are determined by enclosures having walls which are fixed or deformable. Fixed wall enclosures are constituted by measuring cells, whereas moving wall enclosures are constituted by syringes, discontinuous flow systems, peristaltic pumps, and flushing systems.

Other methods implement apportioning systems which make use of properties other than the mechanical properties of enclosures, for example equal period interruptions of a fluid flow taking place at constant speed along a constant section, or interrupting the flow for periods that are related to its speed and section. By way of example, a metering system may be mentioned which uses vanes controlled by a time generator system and acting on a flow of liquid running at constant flow rate.

All of these systems suffer from major drawbacks due to their natures:

measurement errors may take place due to accidental deformations of the walls, to wear of moving walls, to slack and delays in control devices, to sealing defects, or to mechanical accidents which block the system;

errors may also occur in measuring time and in the speed of fluid flow which is a function, inter alia, of the physical properties of the fluid, for example of its viscosity which may vary with temperature.

These errors can naturally be compensated, to some extent, by greater sophistication of the monitoring and control methods, but this is at the expense of simplicity and gives rise to a corresponding increase in cost and in the risk of faulty operation.

The object of the invention is to solve the problem consisting in eliminating or reducing the above-mentioned drawbacks as much as possible, by means of a method and of apparatus for apportioning a primary volume of fluid into secondary volumes in accordance with a predefined relationship.

Another object of the invention is a apportioning method and apparatus making use solely of physical and geometrical properties of bodies that are in contact, such that the accuracy of the apportionment is completely independent of operating conditions, such as the viscosity of the fluid to be apportioned, its temperature, or that of its environment, etc. . . . , for example.

Another object of the invention is a method and apparatus for apportioning a fluid making use of static elements only, thereby avoiding drawbacks due to mechanical wear.

Another object of the invention is a method and an apparatus of this type enabling a fluid to be apportioned by means of a single enclosure so as to eliminate errors due to using multiple enclosures.

To this end, the present invention therefore provides a method of apportioning a primary volume of fluid into a determined number of secondary volumes having a predefined mutual relationship, characterized in that it consists in bringing the primary volume of fluid into an enclosure having a horizontal surface including the same number of fluid evacuation orifices as the desired number of secondary volumes, in selectively preventing or allowing fluid flow through the evacuation orifices simultaneously for all of the orifices, and in ensuring that the fluid is uniformly apportioned between the evacuation orifices by forming a free fluid surface parallel to said horizontal surface including the evacuation orifices, and by said free surface being simultaneously fractioned by the evacuation orifices.

Advantageously, the invention also provides for ensuring that all of the fluid to be apportioned is caused to flow by bringing a propellant fluid into the enclosure, which propellant fluid is not miscible with the fluid to be apportioned.

It will be understood that when the flow of the fluid through the evacuation orifices is prevented, this method makes it possible to form a free fluid surface above the horizontal surface of the enclosure having the evacuation orifices. When the fluid is subsequently allowed to flow simultaneously through the evacuation orifices, the free surface of the fluid moves progressively closer to the evacuation orifices and is fractioned simultaneously by all of the orifices. This gives rise to an interruption in the supply of fluid to said orifices. Preferably, the above-mentioned horizontal surface of the enclosure is formed by the surfaces of the evacuation orifices. This serves to avoid having a more or less well-determined quantity of residual fluid present on the bottom of the enclosure.

In order to further improve the accuracy of the apportionment, the invention provides for reducing said free fluid surface by means of a guide surface disposed in the enclosure in the proximity of the evacuation orifices.

Thus, the area of the free fluid surface may be reduced progressively until it becomes substantially equal to the sum of the areas of the evacuation orifices.

Finally, in order to vary the number of said secondary volumes, the invention also provides for some of them to be selectively closable.

The invention also provides an apparatus for apportioning a primary volume of fluid into a predetermined number of secondary volumes having a predefined mutual relationship, characterized in that it comprises a closed enclosure delimiting a chamber for receiving the primary volume of fluid and including an admission orifice and fluid evacuation orifices, said evacuation orifices being formed in a horizontal surface of said chamber, the number of evacuation orifices corresponding to the desired number of secondary volumes of fluid, and means for selectively preventing or allowing fluid flow through the evacuation orifices to order to form a free fluid surface parallel to the evacuation orifices and to ensure that said free surface is simultaneously fractioned by said orifices.

One of the main advantages of apparatus in accordance with the invention is being particularly simple in design and manufacture, while nevertheless being extremely accurate and (at least to a certain extent) independent of operating conditions such as temperature, pressure, fluid viscosity, etc.

In one mode of implementing the invention, the said means comprise cocks, valves, flaps or the like, mounted in evacuation ducts connected to the evacuation orifices.

In a variant, the said means comprise U-tubes forming fluid evacuation ducts and connected to the evacuation orifices.

The apparatus also includes means for inserting a propellant fluid into the enclosure, said fluid not being miscible with the fluid to be apportioned.

In accordance with another characteristic of the invention, the enclosure includes a geometrical fluid pre-apportioning surface beginning in the vicinity of the admission orifice and terminating in the vicinity of the evacuation orifices. In a preferred embodiment of the invention, the pre-apportioning surface is substantially conical in shape, with its apex being oriented towards the fluid admission orifice, and with its base being in the vicinity of the evacuation orifices.

Preferably a spreader device is associated with the admission orifice and comprises a surface which is parallel to the apex of the pre-apportioning surface and which is disposed in the immediate vicinity thereof.

Finally, the evacuation orifices may be formed at the bottoms of fluid confinement grooves or recesses which are suitable for being completely filled with the fluid to be apportioned, the cross-section of said grooves and/or recesses tapering going towards the evacuation orifices.

The invention will be better understood, and other objects, characteristics and advantages thereof appear more clearly on reading the following description given by way of example and with reference to the accompanying drawings, in which.

Figure 1:
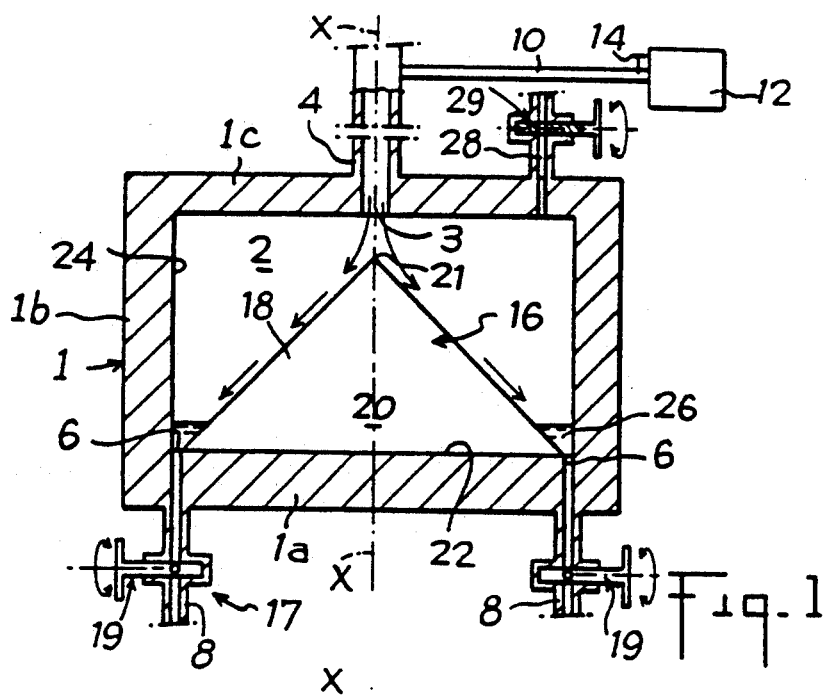
FIG. 1 is a diagrammatic vertical axial section through apparatus in accordance with the invention.

FIG. 1 shows apparatus in accordance with the invention for apportioning a primary volume of a fluid into a determined number of secondary volumes having a predefined mutual relationship. This apparatus comprises a closed enclosure designated by reference 1, delimiting an internal chamber 2 for pre-apportioning the fluid, and including a fluid admission orifice 3, extended by an admission channel 4, and a number of fluid evacuation orifices 6 corresponding to the desired number of secondary volumes, each connected to a corresponding evacuation channel 8.

The pre-apportioning chamber 2 has an axis of symmetry symbolized by line X—X and the evacuation orifices 6 are symmetrically disposed about said axis, and they lie in the same horizontal plane. Fluid guide means 16 are also provided between the admission orifice 3 and the evacuation orifices 6, and means 17 are associated with the orifices 6 or with the channels 8 in order to ensure that the channels 8 are simultaneously and uniformly fed with fluid.

Apparatus in accordance with the invention also preferably includes means for inserting a propellant fluid into the chamber 2 from a supply 12 of propellant fluid which is connected to the admission channel 4 upstream from the admission orifice 3 via a duct 10. The propellant fluid is not miscible with the fluid to be apportioned. A manual or automatic control valve 14 serves to open and close the duct 10. The propellant fluid may therefore be injected under pressure into the chamber 2 in order to oblige the fluid to be apportioned to flow completely via the evacuation orifices 6 and the ducts 8.

It may be observed that it is preferable for the pre-apportioning chamber 2 to be made in such a manner as to contain no horizontal fluid guide surfaces, other than the surfaces of the evacuation orifices 6.

The guide means 16 comprise a flow surface 18 having an axis of symmetry which coincides with the axis X—X of the chamber 2 and which is conical in shape, for example, extending from the vicinity of the admission orifice 3 as far as the evacuation orifices 6 for the purpose of causing the fluid to flow towards said evacuation orifices.

The apex 21 of the cone 20 defining the flow surface 18 lies on the axis of symmetry X—X of the chamber 2, and the base 22 of the cone stands on or constitutes the portion of the wall which forms the bottom of the chamber 2, such that the liquid to be apportioned which is injected via the orifice 3 arrives at the apex 21 of the cone 1 and flows over its surface 18 until it reaches the evacuation orifices 6. These orifices are formed in the bottom 1a of the enclosure 1 and are substantially tangential to the base of the cone 20, lying outside the cone, as shown in FIG. 1.

The above-mentioned means 17 include cocks 19 mounted in the evacuation ducts 8 and arranged to be capable of being opened and closed simultaneously. Instead of using cocks, other equivalent means such as various types of valve could also be used.

The top wall 1c of the enclosure 1 has a vent hole 28 associated with closure means such as a cock 29 or any other equivalent means such as a valve.

The cocks 19 and 29 or the equivalent means are automatically controlled in order to enable particularly simple operation of the apportioning apparatus in accordance with the invention.

Operation is as follows:

With the enclosure 1 being empty of the fluid to be apportioned, the cocks 19 of the evacuation ducts 8 are closed and the cock 29 of the vent hole 28 is opened. A primary volume of fluid to be apportioned is inserted into the chamber 2 via the admission duct 4 and the orifice 3, and it runs over the apex 21 of the cone 20 and is distributed uniformly over the flow surface 18 towards the evacuation orifices 6. Since the cocks 19 are closed, the fluid accumulates in the bottom of the chamber 2 between the conical surface 18 and the inside face 24 of the side wall 1b of the enclosure, thereby forming a sheet 26 of fluid over the evacuation orifices 6. This formation of a sheet 26 corresponds to perfectly uniform distribution of the fluid over the orifices 6.

Once a minimum sheet 26 has been formed over the orifices, all of the cocks 19 of the evacuation ducts 8 may be opened simultaneously in order to allow the fluid to flow in all of the ducts 8.

In order to ensure that all of the fluid to be apportioned has completely flowed out, a propellant fluid under pressure is applied to the enclosure 2 from the source 12 via the valve 14, the duct 10, and the admission orifice 3 in order to exert pressure on the fluid to be apportioned and to force it to pass through the evacuation orifices 6. The propellant fluid may also be used to thrust the primary volume of fluid to be apportioned along the admission duct 4 towards the orifice 3.

It will be understood that even if the fluid to be apportioned is a non-wetting fluid which flows non-uniformly over the conical surface 18, the formation of the sheet 26 of the fluid in the chamber 2 necessarily causes the fluid to be uniformly distributed over the evacuation orifices 6.

It will also be understood that the chamber 2 can continue to be fed with the fluid to be apportioned after the cocks 19 have been opened while the fluid is being evacuated via the ducts 8 so long as a minimum quantity of fluid forms a continuous sheet 26 over the evacuation orifices.

The apportionment of a primary volume of fluid into secondary volumes is extremely accurate, with the beginning of fluid flow in each of the various evacuation channels 8 being synchronized by the cocks 19, and with the end of said flow being determined by the fractioning of the free surface of the fluid sheet 26 by the evacuation orifices 6, which orifices are formed in a horizontal plane parallel to said free surface.

It will also be understood that it is advantageous for the horizontal surface of the chamber 2 in which the evacuation orifices 6 are formed to have an area which is substantially equal to the sum of the areas of the evacuation orifices 6 in order to minimize the residual quantity of fluid which may remain on the bottom of the chamber 2.

The operation of apparatus in accordance with the invention is thus independent of the physical characteristics such as temperature, viscosity, or surface tension or wetting capacity of the fluid to be apportioned.

It is also possible to vary the length or the section of the evacuation duct 8 and the sections of the associated evacuation orifices 6 in order to vary the relative proportions of the secondary volumes.

Further, there is no limit on the quantity of fluid to be apportioned.

Apportioning apparatus in accordance with the invention may therefore be incorporated in any apparatus which meters out fluid by apportioning it. The fluid to be apportioned may be a liquid, or it may be a gas, as explained below.

The fluids concerned may be biological fluids for various processes, and in particular for example, for various reactions, in particular, chemical reactions, or for flushing or washing purposes.

Apparatus in accordance with the invention may also be used for inserting additives or dopes in fuels such as gasoline, heating fuel, or diesel fuel.

Said apparatus may also be used for injecting concentrated flavoring into beverages, for filling bulbs, etc.

Figure 2:
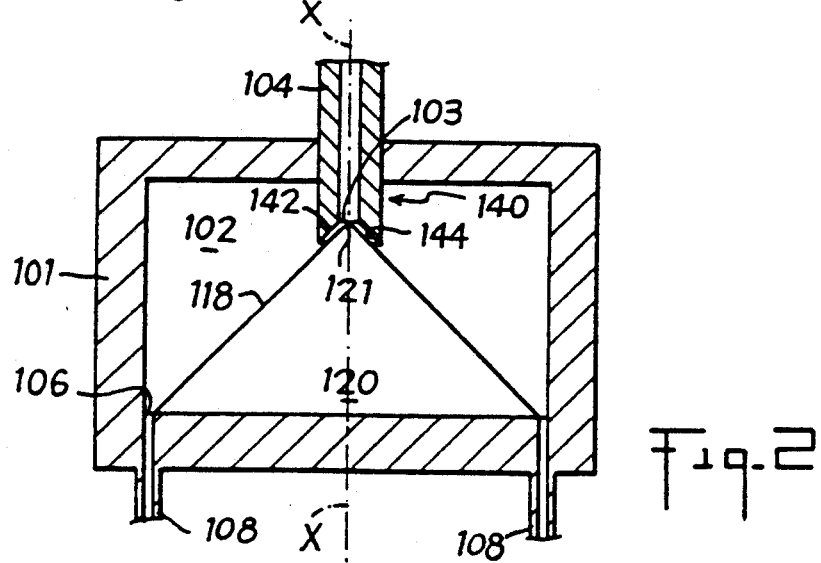
FIG. 2 is a diagram of a second embodiment of the invention.

FIG. 2 shows a variant embodiment of the invention, and identical parts are designated by the same reference numerals as in FIG. 1, plus 100. In this variant embodiment, a spreader device 140 is provided for pouring the fluid to be apportioned over the flow surface 118. This device 140 is constituted by a conical counter-surface 142 disposed at a short distance from the apex 12 of the cone 120, thereby defining a conical passage 144 surrounding the apex of the cone 120 and constraining the fluid to spread out uniformly over the surface 118.

When the fluid to be apportioned is a liquid, the flow of the liquid over the surface 118 takes place without splashing.

Figure 3:
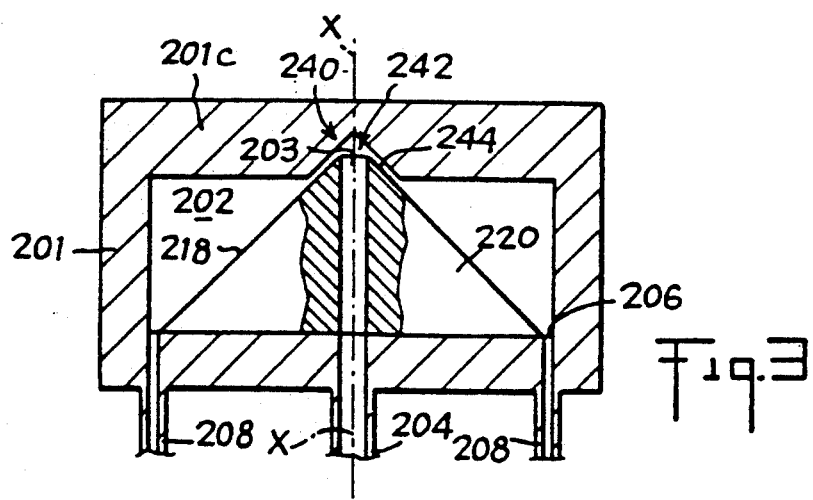
FIG. 3 shows a variant embodiment of said apparatus.

FIG. 3 shows another variant embodiment of apparatus in accordance with the invention, in which items which are identical with or similar to items shows in FIGS. 1 and 2 are designated by references increased by a further 100.

In this embodiment, the admission orifice 203 for the fluid to be apportioned is provided in the body of the cone 220 together with a portion of the admission channel 204. The spreader device 240 is preferably constituted by a conical recess 242 in the top wall 201c of the enclosure 201, thereby providing a small volume 244 in the immediate vicinity of the cone 220. This provides the same advantages as with the embodiment shown in FIG. 2.

Figure 4:
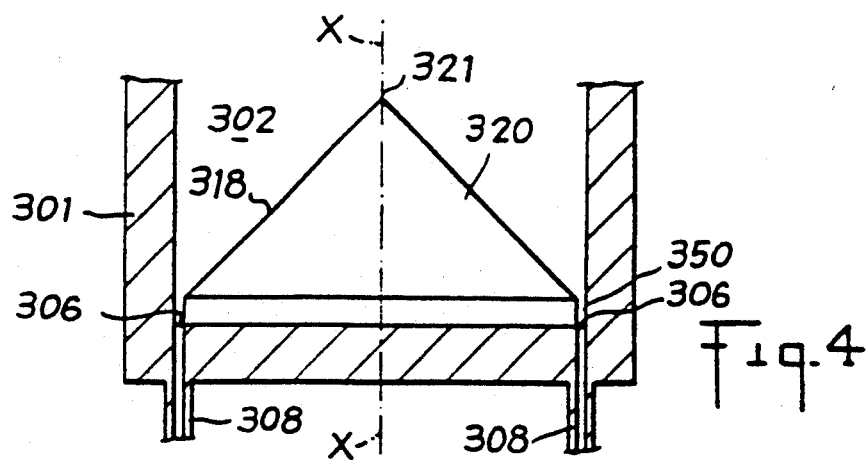
FIG. 4 is a fragmentary vertical axial section through a variant embodiment.

FIG. 4 shows another embodiment of the invention in which items which are identical or similar to those in the preceding figures are designated by the same reference numerals plus a further 100.

In this other embodiment, the chamber 302 includes an annular fluid confinement groove 350 formed over the evacuation orifices 306 and extending around the base of the cone 320. The width of the bottom portion of the groove 350 is equal to the diameter of the evacuation orifices 306. The residual free surface of the fluid to be apportioned contained in said groove is thus substantially equal to the total area of the evacuation orifices 306.

Figure 5:
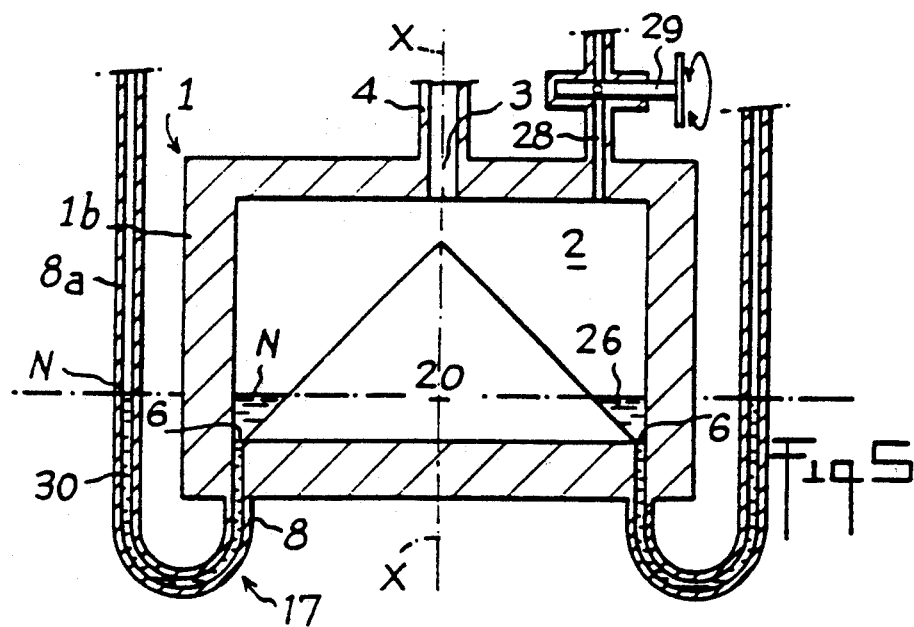
FIG. 5 is a diagrammatic vertical axial section through another variant embodiment.

FIG. 5 shows another embodiment of apportioning apparatus in accordance with the present invention which constitutes a variant of the embodiment shown in FIG. 1, and in which parts or items which are identical with those of the FIG. 1 device are designated by the same references as in FIG. 1.

In this variant embodiment, the means 17 which were used in the FIG. 1 device for synchronizing flow via the evacuation orifices 6 have been replaced by a system of U-tubes 30 which cause the evacuation ducts 8 associated with the evacuation orifices 6 to extend back upwardly.

The outer or upper branch 8a of each evacuation duct 8 extends upwardly to a level which is higher than that of the chamber 2. In this way, when a sheet 26 of liquid to be apportioned has formed in the chamber 2 above the evacuation orifices 6, it finds a level N which reappears in the branches 8a of the evacuation ducts 8. As a result, means are provided in a highly simple manner for preventing uncontrolled flow of the liquid via the orifices 6 and the ducts 8.

Once a primary volume of liquid to be apportioned has been inserted in the chamber 2 and has formed a sheet 26 covering the evacuation orifices 6, the vent hole 28 is closed by the cock 29 and a propellant fluid is brought into the chamber 2 under pressure in order to cause the liquid to be apportioned to flow via the evacuation orifices 6 and the ducts 8. The free surface of the liquid moves down inside the chamber 2 until the liquid has been fractioned uniformly by the evacuation orifices 6.

In a variant, evacuation orifices may be used having walls made of a substance which is not wettable by the fluid to be apportioned, such that the primary volume of the fluid brought into the chamber 2 then forms a sheet 26 over the evacuation orifices until the hydrostatic pressure is high enough to cause flow to occur.

Figure 6:
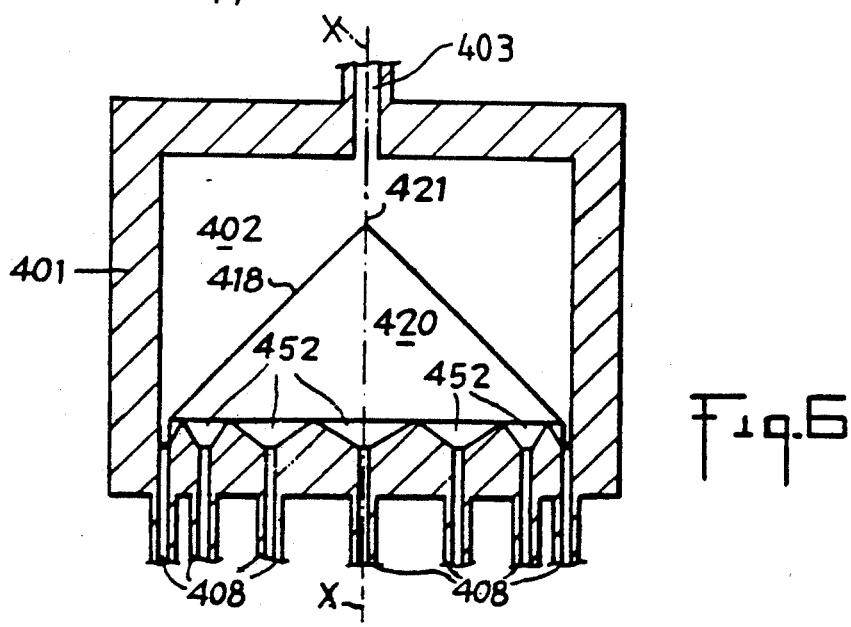
FIG. 6 is a fragmentary view of yet another embodiment.

FIG. 6 shows another embodiment of apparatus in accordance with the invention in the form of a variant of the apparatus shown in FIG. 4, and in which parts or items which are identical are designated by the same reference numerals as in FIG. 4 plus a further 100.

In this variant embodiment, the bottom of the chamber 402 has confinement recesses 452 whose dimensions are such that the fluid to be apportioned fills them completely, given its physical properties. Each of these recesses 452 has a downwardly tapering cross-section and each of them ends in an evacuation duct 408. Preferably, the bases or largest sections of the recesses 452 meet one another so that the bottom of the enclosure 401 has hardly any horizontal surface, thereby ensuring that all of the residual volume of fluid in the chamber 402 can be completely evacuated.

Figure 7:
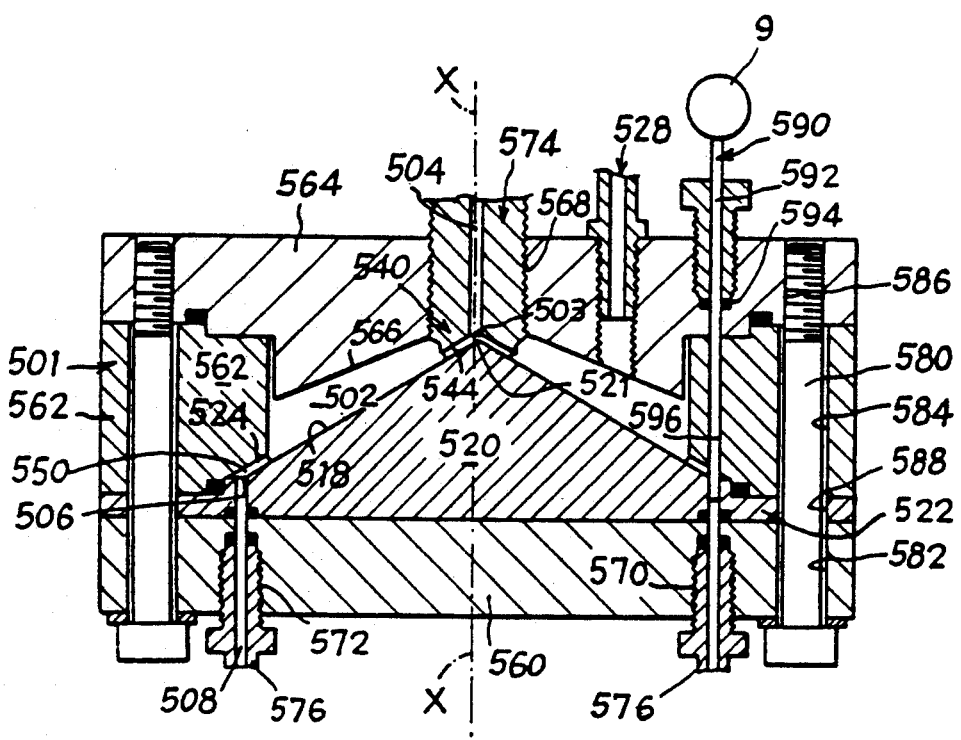
FIG. 7 is a more detailed section view through a practical embodiment of the invention.

FIG. 7 shows a detailed example of an embodiment of apparatus in accordance with the invention. In this figure, parts or items having the same functions as those in the preceding figures are designated by the same reference numerals plus a further 100.

The enclosure 501 is formed by assembling a plurality of distinct parts, whose number and axial symmetry facilitate mechanical fabrication:

a disk-shaped element 560 for constituting the bottom of the enclosure 501 and on which there stands a cone 520 whose large base may be extended horizontally by a plane annular rim 522;

an annular ring 562 forming the vertical side wall 524 of the chamber 502 and including a frustoconical inclined surface 524a at the bottom thereof for the purpose of defining, in conjunction with the inclined surface 518 of the cone 520, confinement recesses 550 or a confinement groove; and a top disk 564 forming the top wall of the enclosure and including frustoconical inclined surfaces 566 above the cone 520 for the purpose of reducing the volume of the chamber 502 if it is to be used with a propellant fluid which is expensive.

Through passages 568, 570, and 572 are formed in the disks 560 and 564 in order to define the admission orifice 503 and the evacuation orifices 506, together with the admission channel 504 and the evacuation channels 508, in particular through intermediate removable parts such as 574 and 576. The disks 560 and 564, the annular ring 562, and the cone 520 may be fixed together by means of threaded rods 580 passing through orifices 582, 584, 586, and 588 respectively formed in the disk 560, the ring 562, the disk 564 and the rim 552 of the cone 520.

Retractable shutter means 590 including rods 592 passing along bores 594 and 596 respectively through the top disk 564 and the annular ring 562 are provided for the purpose of closing the evacuation orifices 506 and adjacent portions of the evacuation channels 508.

The vent 528 is formed by a single part whose base is screwed into a threaded hole in the top disk 564.

Operation is identical to that of the preceding embodiments, with the possibility of closing some of the evacuation ducts 508 in order to vary the number of secondary volumes, as desired.

Figure 8:
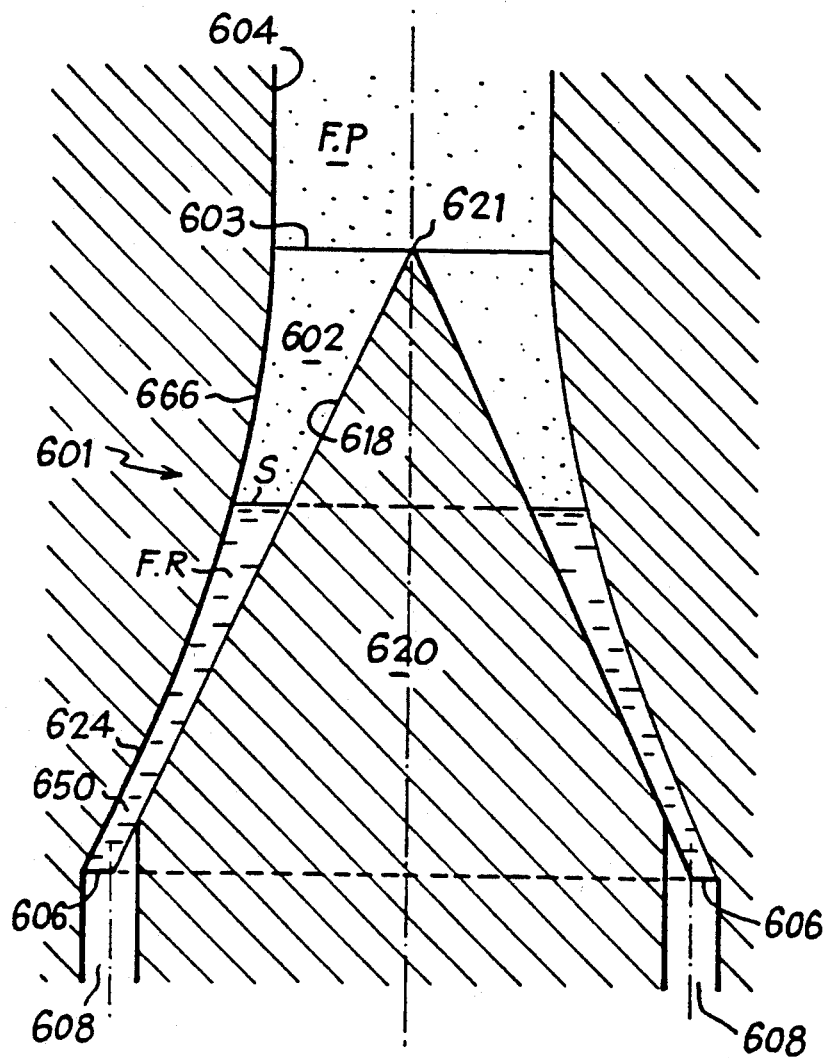
FIG. 8 is a diagrammatic fragmentary axial section view through another variant of the invention.

FIG. 8 shows another embodiment of apportioning apparatus in accordance with the invention, in which parts or items performing the same functions as in FIG. 7 are designated using the same reference numerals plus a further 100.

In this example, the pre-apportioning chamber 602 is formed between the flow wall 618 of a cone 620 having an apex 621 which extends upwardly towards the admission orifice 603 terminating the duct 604, and a surface of revolution 666 having a convex curved profile such that cross-sections through the chamber 602 are substantially equal in area to the area of the admission duct 604 and the admission orifice 603. The top portion of this curved wall 666 is directly connected to the admission duct 604, and its bottom portion is directly connected to the evacuation orifices 606 which are formed in a common horizontal plane and which are associated with evacuation ducts 608. Between the base of the cone 620 and the bottom portion of the curved wall 666, it is also possible to provide fluid confinement recesses 650 as in the embodiments shown in FIGS. 6 and 7.

In the FIG. 8 embodiment, a primary volume of fluid to be apportioned is merely propelled along the admission duct 604 by means of a propellant fluid in order for it to be uniformly apportioned into the desired secondary volumes corresponding to the evacuation orifices 606 and to the channels 608. The accuracy with which the fluid is apportioned results from the fact that there is a single separation surface S between the propellant fluid designated by the letters FP and the fluid to be apportioned designated by the letters FR, said separation surface occupying the entire cross-section of the chamber 602 and behaving like a piston under the effect of pressure from the propellant fluid.

The FIG. 8 embodiment can operate in any position with a fluid to be apportioned in the form of a liquid or a gas.

Naturally, the pressure of the propellant fluid should be determined in such a manner as to avoid setting up any discontinuity at its single separation surface with the fluid to be apportioned. The value of the pressure depends on the physical characteristic of the propellant fluid and of the fluid to be apportioned, and it is easily determined by the person skilled in the art.

In its general form, apportioning apparatus may be used when the fluid to be apportioned is a gas, simply by turning it upsidedown with the evacuation orifices then being at the top of the chamber and the admission orifice being at the bottom, together with any possible vent hole. In this disposition, the propellant fluid is preferably a liquid.

Initially, the enclosure and the evacuation duct are filled with a liquid in which the gas to be apportioned is insoluble, and which has a vapor pressure suitable to avoid polluting the gas.

When the gas to be apportioned is inserted in the enclosure, the vent hole (which is now a drain hole) is opened in order to evacuate the liquid which is progressively replaced by the gas which accumulates beneath the evacuation orifices. When a sufficient volume of gas has been formed in this way, the draining orifice is closed, and the gas flows into the evacuation ducts under pressure from the propellant liquid, displacing any liquid which may have been located therein, until the propellant liquid has refilled the enclosure and the evacuation ducts.

We claim:

1. A method of apportioning a primary volume of fluid into secondary volumes having a predefined mutual relationship by means of an enclosure having a bottom horizontal surface provided with fluid evacuation orifices connected to evacuation ducts, the total area of the said bottom horizontal surface being substantially equal to the sum of the areas of the evacuation orifices, the method comprising bringing the primary volume of fluid into said enclosure and forming a horizontal free fluid surface above the evacuation orifices while preventing the fluid from flowing through the evacuation ducts, and allowing the fluid to simultaneously flow through the evacuation ducts, wherein the free surface of the fluid is simultaneously fractioned by the said evacuation orifices for ensuring that the fluid is uniformly apportioned between the evacuation ducts.

2. A method according to claim 1, further comprising bringing a propellant fluid into the enclosure for ensuring that all of the fluid to be apportioned is caused to flow through the evacuation orifices and the evacuation ducts, wherein said propellant fluid is not miscible with the fluid to be apportioned.

3. A method according to claim 1, further comprising progressively reducing the area of the free fluid surface when the fluid flows through the evacuation orifices and ducts, by means of a guide surface disposed in the enclosure and extending to the evacuation orifices.

4. An apparatus for apportioning a primary volume of fluid into secondary volumes having a predefined mutual relationship, the apparatus comprising a closed enclosure having a chamber for receiving the primary volume of fluid and including a fluid admission orifice and a bottom horizontal surface provided with fluid evacuation orifices connected to evacuation ducts, the total area of the said bottom horizontal surface being substantially equal to the sum of the areas of the evacuation orifices, means for preventing the fluid from flow through the evacuation ducts when the primary volume of fluid is brought into the said chamber and for allowing the fluid to simultaneously flow through the evacuation ducts in order to form a horizontal free fluid surface above the evacuation orifices and for ensuring that said free fluid surface is simultaneously fractioned by the evacuation orifices.

5. Apparatus according to claim 4, wherein the said means for preventing comprise cocks or valves mounted in the evacuation ducts.

6. Apparatus according to claim 4, wherein the evacuation ducts are U-tubes.

7. Apparatus according to claim 4, comprising means for feeding a propellant fluid into said chamber, said propellant fluid being not miscible with the fluid to be apportioned.

8. An apparatus according to claim 4, wherein the enclosure includes a geometrical fluid guiding surface disposed in said chamber between the admission orifice and the evacuation orifices.

9. An apparatus according to claim 8, wherein the fluid guiding surface is substantially conical in shape and has an apex oriented towards the admission orifice and a base located in the vicinity of the evacuation orifices.

10. An apparatus according to claim 9, comprising a spreader device located in said chamber above the fluid guiding surface, said spreader device having a surface parallel to the apex of the fluid guiding surface and disposed in the immediate vicinity thereof.

11. An apparatus according to claim 4, wherein the evacuation orifices are connected to the evacuation ducts by recesses of tapering cross-section.

12. An apparatus according to claim 4, wherein the said enclosure comprises a vent hole opening out into said chamber and means for closing said vent hole.

13. An apparatus according to claim 4, wherein the said enclosure comprises: a disk-shaped element forming a bottom wall of the enclosure and including the evacuation orifices and the evacuation ducts; a conical element disposed on the bottom wall; an annular element forming a side wall of the enclosure and including a frustoconical inside surface extending above the evacuation orifices; a top element in the form of a disk including the admission orifice and constituting a top of the enclosure; and fixing means comprising bolts passing through the above-mentioned elements to hold them together in sealed manner.

14. Apparatus according to claim 4, wherein the said chamber is between an internal conical surface and on outer convex surface of revolution and has a cross-section of constant area substantially equal to that of the admission orifice.

* * * * *